(12) United States Patent
Holton et al.

(10) Patent No.: US 7,160,919 B2
(45) Date of Patent: Jan. 9, 2007

(54) C7 LACTYLOXY-SUBSTITUTED TAXANES

(75) Inventors: Robert A. Holton, Tallahassee, FL (US); Hyeong Baik Kim, Newark, DE (US)

(73) Assignee: Florida State University Research Foundation, Inc., Tallahassee, FL (US)

( * ) Notice: Subject to any disclaimer, the term of this patent is extended or adjusted under 35 U.S.C. 154(b) by 0 days.

(21) Appl. No.: 11/071,912

(22) Filed: Mar. 4, 2005

(65) Prior Publication Data

US 2005/0209311 A1 Sep. 22, 2005

Related U.S. Application Data

(60) Provisional application No. 60/550,712, filed on Mar. 5, 2004.

(51) Int. Cl.
| | |
|---|---|
| A01N 43/02 | (2006.01) |
| A61K 31/335 | (2006.01) |
| C07D 305/00 | (2006.01) |
| C07D 407/00 | (2006.01) |
| C07D 493/00 | (2006.01) |

(52) U.S. Cl. ...................... 514/449; 549/510
(58) Field of Classification Search ................ 549/472, 549/510; 514/449, 461
See application file for complete search history.

(56) References Cited

U.S. PATENT DOCUMENTS

| | | |
|---|---|---|
| 4,960,790 A | 10/1990 | Stella et al. |
| 5,175,315 A | 12/1992 | Holton |
| 5,200,534 A | 4/1993 | Rao |
| 5,227,400 A | 7/1993 | Holton et al. |
| 5,243,045 A | 9/1993 | Holton et al. |
| 5,248,796 A | 9/1993 | Chen et al. |
| 5,283,253 A | 2/1994 | Holton et al. |
| 5,319,112 A | 6/1994 | Kingston et al. |
| 5,350,866 A | 9/1994 | Holton et al. |
| 5,352,806 A | 10/1994 | Gunawardana et al. |
| 5,415,869 A | 5/1995 | Straubinger et al. |
| 5,422,364 A | 6/1995 | Nicolaou et al. |
| 5,430,160 A | 7/1995 | Holton |
| 5,489,601 A | 2/1996 | Holton et al. |
| 5,530,020 A | 6/1996 | Gunawardana et al. |
| 5,567,614 A | 10/1996 | Patel et al. |
| 5,614,645 A | 3/1997 | Kingston et al. |
| 5,714,513 A | 2/1998 | Holton et al. |
| 5,721,268 A | 2/1998 | Holton et al. |
| 5,767,297 A | 6/1998 | Mandai et al. |
| 5,780,653 A | 7/1998 | Tao et al. |
| 5,811,452 A | 9/1998 | Ojima et al. |
| 5,879,929 A | 3/1999 | Patel |
| 5,912,264 A | 6/1999 | Wittman et al. |
| 5,965,739 A | 10/1999 | Kelly et al. |
| 6,136,988 A | 10/2000 | Murray et al. |
| 6,160,135 A | 12/2000 | Bouchard et al. |
| 6,576,636 B1 | 6/2003 | Webb et al. |
| 6,673,833 B1 | 1/2004 | Holton |

FOREIGN PATENT DOCUMENTS

| | | |
|---|---|---|
| EP | 0 558 959 B1 | 9/1993 |
| EP | 0 590 267 A2 | 4/1994 |
| EP | 0 629 701 A1 | 12/1994 |
| EP | 0 747 385 B1 | 12/1996 |
| WO | WO 90/10443 A1 | 9/1990 |
| WO | WO 93/02065 A1 | 2/1993 |
| WO | WO 94/14787 A1 | 7/1994 |
| WO | 94/21250 * | 9/1994 |
| WO | WO 95/11241 A1 | 4/1995 |
| WO | WO 95/13053 A1 | 5/1995 |
| WO | WO 97/09979 A1 | 3/1997 |
| WO | WO 97/42181 A1 | 11/1997 |
| WO | WO 97/44026 A1 | 11/1997 |
| WO | WO 97/44063 A1 | 11/1997 |
| WO | WO 99/09021 A1 | 2/1999 |
| WO | WO 00/01366 A1 | 1/2000 |
| WO | WO 00/78707 A1 | 12/2000 |
| WO | WO 01/25223 A1 | 4/2001 |
| WO | WO 01/57013 A1 | 8/2001 |
| WO | WO 01/57027 A1 | 8/2001 |
| WO | WO 01/68089 A1 | 9/2001 |

OTHER PUBLICATIONS

Safarpour, H., et al., "Concentration of Milataxel (MAC-321, TL00139) and its Major Metabolite (M-10) in Xenograft Tumors from Mice Dosed Orally and Intravenously," Abstract #512, 97th Annual Meeting of the American Association for Cancer Research, Apr. 1-5, 2006, Washington, D.C.

(Continued)

*Primary Examiner*—Thomas McKenzie
*Assistant Examiner*—Niloofar Rahmani
(74) *Attorney, Agent, or Firm*—Senniger Powers

(57) ABSTRACT

A taxane having the formula:

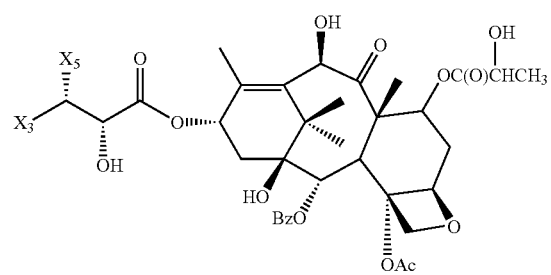

wherein $X_3$ is furyl, $X_5$ is t-butoxycarbonyl, Bz is benzoyl, and Ac is acetyl.

19 Claims, No Drawings

OTHER PUBLICATIONS

Yang, Li-Xi, et al., "Enhanced Apoptotic Effects of Novel Paclitaxel Analogs on NCI/ADR-RES Breast Cancer Cells," AntiCancer Research 23:3295-3302 (2003), San Francisco, California.

Sampath, D., et al., "MAC-321, A Novel Taxane With Greater Efficacy Than Paclitaxel and Docetaxel In Vitro and In Vivo," Molecular Cancer Therapeutics, 2003, pp. 873-884.

International Search Report, PCT/US05/07100, from the International Searching Authority dated Jun. 21, 2005.

Deutsch, H.M., et al., "Synthesis of Congeners and Prodrugs. 3. Water-Soluble Prodrugs of Taxol with Potent Antitumor Activity," Journal of Medicinal Chemistry, 1989, pp. 788-792, vol. 32, No. 4.

Dubois, J., "Fluorescent and Biotinylated Analogues of Docetaxel: Synthesis and Biological Evaluation," Bioorganic & Medicinal Chemistry, 1995, pp. 1357-1368, vol. 3, No. 10.

European Search Report for EP 01 11 8729 dated Oct. 30, 2001.

Ferlini, C., et al., "Antitumor Activity of Novel Taxanes that Act at the Same Time as Cytotoxic Agents and P-Glycoprotein Inhibitors," British Journal of Cancer, 2000, pp. 1762-1768, vol. 83, No. 12.

Guenard, D., et al., "Effects of the Hydrophobicity of Taxoids on their Interaction with Tubulin," Bioorganic & Medicinal Chemistry, 2000, pp. 145-156, vol. 8.

Gueritte-Voégelein, F., et al., "Relationships Between the Structure of Taxol Analogues and Their Antimitotic Activity," Journal of Medicinal Chemistry, 1991, pp. 992-998, vol. 34, No. 3.

Hungarian Search Report from Application No. P0103247 dated Dec. 14, 2004.

International Search Report from PCT Application No. PCT/US01/03385 dated Jun. 11, 2001.

Ishihara, K., et al., "Scandium Trifluoromethanesulfonate as an Extremely Active Acylation Catalyst," Journal of the American Chemical Society, 1995, pp. 4413-4414, vol. 117, No. 15.

Kingston, D.G.I., et al., "The Chemistry of Taxol, A Clinically Useful Anticancer Agent," Journal of Natural Products, Jan.-Feb. 1990, pp. 1-12, vol. 53, No. 1.

Klein, L.L., "Synthesis of 9-Dihydrotaxol: A Novel Bioactive Taxane," Tetrahedron Letters, 1993, pp. 2047-2050, vol. 34, No. 13, Pergamon Press, Ltd.

Liang, X., et al., "Synthesis and Biological Evaluation of Paclitaxel Analogs Modified in Ring C," Tetrahedron Letters, 1995, pp. 2901-2904, vol. 36, No. 17, Pergamon Press, Ltd.

Mellado, W., et al., "Preparation and Biological Activity of Taxol Acetates," Biochemical and Biophysical Research Communications, Oct. 30, 1984, pp. 329-336, vol. 124, No. 2.

Ojima, I., et al., "New Photoaffinity Analogs of Paclitaxel," Bioorganic & Medicinal Chemistry Letters, 1999, pp. 1189-1194, vol. 9.

Patel, R.N., "Tour de Paclitaxel: Biocatalysis for Semisynthesis," Annual Review of Microbiology, 1998, pp. 361-395, vol. 52.

Shi, B.X., et al., "Studies on the Quantitative Structure-activity Relationships of Paclitaxel Analogues," Chemical Journal of Chinese Universities, 2000, pp. 401-406. vol. 21, No. 3.

Straubinger, R.M., et al., "Pharmacology and Antitumor Effect of Novel Paclitaxel Formulations," Chapter 8, ACS Symposium Series 583, 207th National Meeting of the American Chemical Society, 1994, pp. 111-123.

Suffness, M., "Chapter 32. Taxol: From Discovery to Therapeutic Use," Annual Reports in Medicinal Chemistry, 1993, pp. 305-314, vol. 28.

Vyas, D.M., et al., "Phosphatase-Activated Prodrugs of Paclitaxel," Chapter 9, ACS Symposium Series 583, 207th National Meeting of the American Chemical Society, 1994, pp. 124-137.

* cited by examiner

C7 LACTYLOXY-SUBSTITUTED TAXANES

CROSS-REFERENCE TO RELATED APPLICATIONS

This application claims priority from U.S. Provisional Application Ser. No. 60/550,712 filed Mar. 5, 2004 which is hereby incorporated by reference in its entirety.

BACKGROUND OF THE INVENTION

The present invention is directed to novel taxanes having utility as antitumor agents.

The taxane family of terpenes, of which baccatin III and taxol, also commonly referred to as paclitaxel, are members, has been the subject of considerable interest in both the biological and chemical arts. Taxol itself is employed as a cancer chemotherapeutic agent and possesses a broad range of tumor-inhibiting activity. Taxol has a 2'R, 3'S configuration and the following structural formula:

wherein Ac is acetyl.

Colin et al. reported in U.S. Pat. No. 4,814,470 that certain taxol analogs have an activity significantly greater than that of taxol. One of these analogs, commonly referred to as docetaxel (Taxotere®), has the following structural formula:

Although taxol and docetaxel are useful chemotherapeutic agents, there are limitations on their effectiveness, including limited efficacy against certain types of cancers and toxicity to subjects when administered at various doses. Accordingly, a need remains for additional chemotherapeutic agents with improved efficacy and less toxicity.

SUMMARY OF THE INVENTION

Among the various aspects of the present invention, therefore, is a taxane which compares favorably to taxol and docetaxel with respect to toxicity and to efficacy as an anti-tumor agent. The present invention is further directed to formulations incorporating this taxane, and to methods of treatment using this taxane.

In general, the taxane of the present invention is characterized by a C(7) lactyloxy substituent and corresponds to Formula (1):

wherein
  $R_7$ is lactyloxy;
  $X_3$ is furyl;
  $X_5$ is t-butoxycarbonyl; and
  Ac is acetyl.

The taxane of Formula I may be, for example, in the form of an isolate, crystal or other solid.

The present invention is further directed to pharmaceutical compositions comprising the taxane of Formula I and at least one pharmaceutically acceptable carrier. The pharmaceutical composition may be, for example, in a dosage unit form wherein the dosage unit comprises the taxane in a crystalline or liquid form.

The present invention is further directed to a method of preparing a pharmaceutical composition. In such a method, for example, the taxane is crystallized from a solution. Alternatively, or in addition, the taxane is an admixture with a pharmaceutically acceptable carrier.

The present invention is further directed to a method of inhibiting tumor growth in a mammal. The method comprises administering a therapeutically effective amount of a pharmaceutical composition comprising the taxane and a pharmaceutically acceptable carrier.

Other aspects and features of this invention will be in part apparent and in part pointed out hereinafter.

DETAILED DESCRIPTION OF THE PREFERRED EMBODIMENTS

The C(7) lactyloxy substituent of the taxanes of the present invention include a chiral center and thus, the taxanes may exist as the R diastereomer, the S diastereomer or a mixture of the R and S diastereomers. Each of these, as well as the salts, enantiomers, and tautomers of the compounds of Formula I are within the scope of the present invention. For example, in one embodiment, the taxane is 7-((S)-(−)-2-hydroxyloxypropionyl)-2-furyl-docetaxel. In another embodiment, the taxane is 7-((R)-(+)-2-hydroxyloxypropionyl)-2-furyl-docetaxel. These diastereomers may be present in a racemic or optically active mixture. Alternatively, one of these diastereomers may be present in a composition having an essential absence of the other diastereomer (e.g., a molar ratio of at least 5:1, 10:1 or even 20:1 of one of the two diastereomers relative to the other, respectively).

The taxanes of the present invention are useful for inhibiting tumor growth in mammals including humans and are preferably administered in the form of a pharmaceutical composition comprising an effective antitumor amount of a compound of the instant invention in combination with at least one pharmaceutically or pharmacologically acceptable carrier. The carrier, also known in the art as an excipient, vehicle, auxiliary, adjuvant, or diluent, is any substance which is pharmaceutically inert, confers a suitable consistency or form to the composition, and does not diminish the therapeutic efficacy of the taxane. The carrier is "pharmaceutically or pharmacologically acceptable" if it does not produce an adverse, allergic or other untoward reaction when administered to a mammal or human, as appropriate.

Pharmaceutical compositions containing a taxane of the present invention may be formulated in any conventional manner. Proper formulation is dependent upon the route of administration chosen. The compositions of the invention can be formulated for any route of administration so long as the target tissue is available via that route. Suitable routes of administration include, but are not limited to, oral, parenteral (e.g., intravenous, intra arterial, subcutaneous, rectal, subcutaneous, intramuscular, intraorbital, intracapsular, intraspinal, intraperitoneal, or intrasternal), topical (nasal, transdermal, intraocular), intravesical, intrathecal, enteral, pulmonary, intralymphatic, intracavital, vaginal, transurethral, intradermal, aural, intramammary, buccal, orthotopic, intratracheal, intralesional, percutaneous, endoscopical, transmucosal, sublingual and intestinal administration.

Pharmaceutically acceptable carriers for use in the compositions of the present invention are well known to those of ordinary skill in the art and are selected based upon a number of factors: the particular taxane used, and its concentration, stability and intended bioavailability; the disease, disorder or condition being treated with the composition; the subject, its age, size and general condition; and the route of administration. Suitable carriers are readily determined by one of ordinary skill in the art (see, for example, J. G. Nairn, in: *Remington's Pharmaceutical Science* (A. Gennaro, ed.), Mack Publishing Co., Easton, Pa., (1985), pp. 1492–1517, the contents of which are incorporated herein by reference).

The compositions may be formulated as tablets, dispersible powders, pills, capsules, gelcaps, caplets, gels, liposomes, granules, solutions, suspensions, emulsions, syrups, elixirs, troches, dragees, lozenges, or any other dosage form which can be administered orally. Techniques and compositions for making oral dosage forms useful in the present invention are described in the following references: 7 *Modern Pharmaceutics,* Chapters 9 and 10 (Banker & Rhodes, Editors, 1979); Lieberman et al., *Pharmaceutical Dosage Forms: Tablets* (1981); and Ansel, *Introduction to Pharmaceutical Dosage Forms* 2nd Edition (1976).

In general, compositions for oral administration comprise an effective antitumor amount of the taxane in a pharmaceutically acceptable carrier. Suitable carriers for solid dosage forms include sugars, starches, and other conventional substances including lactose, talc, sucrose, gelatin, carboxymethylcellulose, agar, mannitol, sorbitol, calcium phosphate, calcium carbonate, sodium carbonate, kaolin, alginic acid, acacia, corn starch, potato starch, sodium saccharin, magnesium carbonate, tragacanth, microcrystalline cellulose, colloidal silicon dioxide, croscarmellose sodium, talc, magnesium stearate, and stearic acid. Further, such solid dosage forms may be uncoated or may be coated by known techniques, e.g., to delay disintegration and absorption.

The taxane may also be formulated for parenteral administration, e.g., formulated for injection via intravenous, intra arterial, rectal, subcutaneous, intramuscular, intraorbital, intracapsular, intraspinal, intraperitoneal, or intrasternal routes. In general, compositions for parenteral administration comprise an effective antitumor amount of the taxane in a pharmaceutically acceptable carrier. Dosage forms suitable for parenteral administration include solutions, suspensions, dispersions, emulsions or any other dosage form which can be administered parenterally. Techniques and compositions for making parenteral dosage forms are known in the art.

Suitable carriers used in formulating liquid dosage forms for oral or parenteral administration include nonaqueous, pharmaceutically-acceptable polar solvents such as oils, alcohols, amides, esters, ethers, ketones, hydrocarbons and mixtures thereof, as well as water, saline solutions, dextrose solutions (e.g., DW5), electrolyte solutions, or any other aqueous, pharmaceutically acceptable liquid.

Suitable nonaqueous, pharmaceutically-acceptable polar solvents include, but are not limited to, alcohols (e.g., α-glycerol formal, β-glycerol formal, 1,3-butyleneglycol, aliphatic or aromatic alcohols having 2–30 carbon atoms such as methanol, ethanol, propanol, isopropanol, butanol, t-butanol, hexanol, octanol, amylene hydrate, benzyl alcohol, glycerin (glycerol), glycol, hexylene glycol, tetrahydrofurfuryl alcohol, lauryl alcohol, cetyl alcohol, or stearyl alcohol, fatty acid esters of fatty alcohols such as polyalkylene glycols (e.g., polypropylene glycol, polyethylene glycol), sorbitan, sucrose and cholesterol); amides (e.g., dimethylacetamide (DMA), benzyl benzoate DMA, dimethylformamide, N-(β-hydroxyethyl)-lactamide, N,N-dimethylacetamide-amides, 2-pyrrolidinone, 1-methyl-2-pyrrolidinone, or polyvinylpyrrolidone); esters (e.g., 1-methyl-2-pyrrolidinone, 2-pyrrolidinone, acetate esters such as monoacetin, diacetin, and triacetin, aliphatic or aromatic esters such as ethyl caprylate or octanoate, alkyl oleate, benzyl benzoate, benzyl acetate, dimethylsulfoxide (DMSO), esters of glycerin such as mono, di, or tri-glyceryl citrates or tartrates, ethyl benzoate, ethyl acetate, ethyl carbonate, ethyl lactate, ethyl oleate, fatty acid esters of sorbitan, fatty acid derived PEG esters, glyceryl monostearate, glyceride esters such as mono, di, or tri-glycerides, fatty acid esters such as isopropyl myristate, fatty acid derived PEG esters such as PEG-hydroxyoleate and PEG-hydroxystearate, N-methyl pyrrolidinone, pluronic 60, polyoxyethylene sorbitol oleic polyesters such as poly(ethoxylated)$_{30-60}$ sorbitol poly(oleate)$_{2-4}$, poly(oxyethylene)$_{15-20}$ monooleate, poly(oxyethylene)$_{15-20}$ mono 12-hydroxystearate, and poly(oxyethylene)$_{15-20}$ mono ricinoleate, polyoxyethylene sorbitan esters such as polyoxyethylene-sorbitan monooleate, polyoxyethylene-sorbitan monopalmitate, polyoxyethylene-sorbitan monolaurate, polyoxyethylene-sorbitan monostearate, and Polysorbate® 20, 40, 60 or 80 from ICI Americas, Wilmington, Del., polyvinylpyrrolidone, alkyleneoxy modified fatty acid esters such as polyoxyl 40 hydrogenated castor oil and polyoxyethylated castor oils (e.g., Cremophor® EL solution or Cremophor® RH 40 solution), saccharide fatty acid esters (i.e., the condensation product of a monosaccharide (e.g., pentoses such as ribose, ribulose, arabinose, xylose, lyxose and xylulose, hexoses such as glucose, fructose, galactose, mannose and sorbose, trioses, tetroses, heptoses, and octoses), disaccharide (e.g., sucrose, maltose, lactose and trehalose) or oligosaccharide or mixture thereof with a $C_4$–$C_{22}$ fatty acid(s)(e.g., saturated fatty acids such as caprylic acid, capric acid, lauric acid, myristic acid, palmitic acid and stearic acid, and unsaturated fatty acids such as palmitoleic acid, oleic acid, elaidic acid, erucic acid and linoleic acid)), or steroidal esters); alkyl, aryl, or cyclic ethers having 2–30 carbon atoms (e.g., diethyl ether, tetrahydrofuran, dimethyl isosorbide, diethylene glycol monoethyl ether); glycofurol (tetrahydrofurfuryl alcohol polyethylene glycol ether); ketones having 3–30 carbon atoms (e.g., acetone, methyl ethyl ketone, methyl isobutyl ketone); aliphatic, cycloaliphatic or aromatic hydrocarbons having 4–30 carbon atoms (e.g., benzene, cyclohexane, dichloromethane, dioxolanes, hexane, n-decane, n-dodecane, n-hexane, sulfolane, tetramethylenesulfon, tetramethylenesulfoxide, toluene, dimethylsulfoxide (DMSO), or tetramethylenesulfoxide); oils of mineral, vegetable, animal, essential or synthetic origin (e.g., mineral oils such as aliphatic or wax-based hydrocarbons, aromatic hydrocarbons, mixed aliphatic and aromatic based hydrocarbons, and refined paraffin oil, vegetable oils such as linseed, tung, safflower, soybean, castor, cottonseed, groundnut, rapeseed, coconut, palm, olive, corn, corn germ, sesame, persic and peanut oil and glycerides such as mono-, di- or triglycerides, animal oils such as fish, marine, sperm, cod-liver, haliver, squalene, squalane, and shark liver oil, oleic oils, and polyoxyethylated castor oil); alkyl or aryl halides having 1–30 carbon atoms and optionally more than one halogen substituent; methylene chloride; monoethanolamine; petroleum benzin; trolamine; omega-3 polyunsaturated fatty acids (e.g., alpha-linolenic acid, eicosapentaenoic acid, docosapentaenoic acid, or docosahexaenoic acid); polyglycol ester of 12-hydroxystearic acid and polyethylene glycol (Solutol® HS-15, from BASF, Ludwigshafen, Germany); polyoxyethylene glycerol; sodium laurate; sodium oleate; or sorbitan monooleate.

Other pharmaceutically acceptable solvents are well known to those of ordinary skill in the art, and are identified in *The Chemotherapy Source Book* (Williams & Wilkens Publishing), *The Handbook of Pharmaceutical Excipients,* (American Pharmaceutical Association, Washington, D.C., and The Pharmaceutical Society of Great Britain, London, England, 1968), *Modern Pharmaceutics,* (G. Banker et al., eds., 3d ed.)(Marcel Dekker, Inc., New York, N.Y., 1995), *The Pharmacological Basis of Therapeutics,* (Goodman & Gilman, McGraw Hill Publishing), *Pharmaceutical Dosacie Forms,* (H. Lieberman et al., eds., )(Marcel Dekker, Inc., New York, N.Y., 1980), *Remington's Pharmaceutical Sciences* (A. Gennaro, ed., 19th ed.)(Mack Publishing, Easton, Pa., 1995), *The United States Pharmacopeia* 24, *The National Formulary* 19, (National Publishing, Philadelphia, Pa., 2000), A. J. Spiegel et al., and Use of Nonaqueous Solvents in Parenteral Products, JOURNAL OF PHARMACEUTICAL SCIENCES, Vol. 52, No. 10, pp. 917–927 (1963).

Preferred solvents include those known to stabilize taxanes, such as oils rich in triglycerides, for example, safflower oil, soybean oil or mixtures thereof, and alkyleneoxy modified fatty acid esters such as polyoxyl 40 hydrogenated castor oil and polyoxyethylated castor oils (e.g., Cremophor® EL solution or Cremophor® RH 40 solution). Commercially available triglyceride-rich oils include Intralipid® emulsified soybean oil (Kabi-Pharmacia Inc., Stockholm, Sweden), Nutralipid ® emulsion (McGaw, Irvine, Calif.), Liposyn® II 20% emulsion (a 20% fat emulsion solution containing 100 mg safflower oil, 100 mg soybean oil, 12 mg egg phosphatides, and 25 mg glycerin per ml of solution; Abbott Laboratories, Chicago, Ill.), Liposyn® III 2% emulsion (a 2% fat emulsion solution containing 100 mg safflower oil, 100 mg soybean oil, 12 mg egg phosphatides, and 25 mg glycerin per ml of solution; Abbott Laboratories, Chicago, Ill.), natural or synthetic glycerol derivatives containing the docosahexaenoyl group at levels between 25% and 100% by weight based on the total fatty acid content (Dhasco® (from Martek Biosciences Corp., Columbia, Md.), DHA Maguro® (from Daito Enterprises, Los Angeles, Calif.), Soyacal®, and Travemulsion®. Ethanol is a preferred solvent for use in dissolving the taxane to form solutions, emulsions, and the like.

Additional minor components can be included in the compositions of the invention for a variety of purposes well known in the pharmaceutical industry. These components generally impart properties which enhance retention of the taxane at the site of administration, protect the stability of the composition, control the pH, facilitate processing of the taxane into pharmaceutical formulations, and the like. Preferably, each of these components is individually present in less than about 15 weight % of the total composition, more preferably less than about 5 weight %, and most preferably less than about 0.5 weight % of the total composition. Some components, such as fillers or diluents, can constitute up to 90 wt. % of the total composition, as is well known in the formulation art. Such additives include cryoprotective agents for preventing reprecipitation of the taxane, surface active, wetting or emulsifying agents (e.g., lecithin, polysorbate-80, Tween® 80, pluronic 60, polyoxyethylene stearate, and polyethoxylated castor oils), preservatives (e.g., ethyl-p-hydroxybenzoate), microbial preservatives (e.g., benzyl alcohol, phenol, m-cresol, chlorobutanol, sorbic acid, thimerosal and paraben), agents for adjusting pH or buffering agents (e.g., acids, bases, sodium acetate, sorbitan monolaurate), agents for adjusting osmolarity (e.g., glycerin), thickeners (e.g., aluminum monostearate, stearic acid, cetyl alcohol, stearyl alcohol, guar gum, methyl cellulose, hydroxypropylcellulose, tristearin, cetyl wax esters, polyethylene glycol), colorants, dyes, flow aids, non-volatile silicones (e.g., cyclomethicone), clays (e.g., bentonites), adhesives, bulking agents, flavorings, sweeteners, adsorbents, fillers (e.g., sugars such as lactose, sucrose, mannitol, or sorbitol, cellulose, or calcium phosphate), diluents (e.g., water, saline, electrolyte solutions), binders (e.g., starches such as maize starch, wheat starch, rice starch, or potato starch, gelatin, gum tragacanth, methyl cellulose, hydroxypropyl methylcellulose, sodium carboxymethyl cellulose, polyvinylpyrrolidone, sugars, polymers, acacia), disintegrating agents (e.g., starches such as maize starch, wheat starch, rice starch, potato starch, or carboxymethyl starch, cross-linked polyvinyl pyrrolidone, agar, alginic acid or a salt thereof such as sodium alginate, croscarmellose sodium or crospovidone), lubricants (e.g., silica, talc, stearic acid or salts thereof such as magnesium stearate, or polyethylene glycol), coating agents (e.g., concentrated sugar solutions including gum arabic, talc, polyvinyl pyrrolidone, carbopol gel, polyethylene glycol, or titanium dioxide), and antioxidants (e.g., sodium metabisulfite, sodium bisulfite, sodium sulfite, dextrose, phenols, and thiophenols).

Dosage form administration by these routes may be continuous or intermittent, depending, for example, upon the patient's physiological condition, whether the purpose of the administration is therapeutic or prophylactic, and other factors known to and assessable by a skilled practitioner.

Dosage and regimens for the administration of the pharmaceutical compositions of the invention can be readily determined by those with ordinary skill in treating cancer. It is understood that the dosage of the taxanes will be dependent upon the age, sex, health, and weight of the recipient, kind of concurrent treatment, if any, frequency of treatment, and the nature of the effect desired. For any mode of administration, the actual amount of taxane delivered, as well as the dosing schedule necessary to achieve the advantageous effects described herein, will also depend, in part, on such factors as the bioavailability of the taxane, the disorder being treated, the desired therapeutic dose, and other factors that will be apparent to those of skill in the art. The dose administered to an animal, particularly a human, in the context of the present invention should be sufficient to effect the desired therapeutic response in the animal over a reasonable period of time. Preferably, an effective amount of the taxane, whether administered orally or by another route, is any amount which would result in a desired therapeutic response when administered by that route. Preferably, the compositions for oral administration are prepared in such a way that a single dose in one or more oral preparations contains at least 20 mg of the taxane per $m^2$ of patient body surface area, or at least 50, 100, 150, 200, 300, 400, or 500 mg of the taxane per $m^2$ of patient body surface area, wherein the average body surface area for a human is 1.8 $m^2$. Preferably, a single dose of a composition for oral administration contains from about 20 to about 600 mg of the taxane per $m^2$ of patient body surface area, more preferably from about 25 to about 400 $mg/m^2$, even more preferably, from about 40 to about 300 $mg/m^2$, and even more preferably from about 50 to about 200 $mg/m^2$. Preferably, the compositions for parenteral administration are prepared in such a way that a single dose contains at least 20 mg of the taxane per $m^2$ of patient body surface area, or at least 40, 50, 100, 150, 200, 300, 400, or 500 mg of the taxane per $m^2$ of patient body surface area. Preferably, a single dose in one or more parenteral preparations contains from about 20 to about 500 mg of the taxane per $m^2$ of patient body surface area, more preferably from about 40 to about 400 $mg/m^2$, and even more preferably, from about 60 to about 350 $mg/m^2$. However, the dosage may vary depending on the dosing schedule which can be adjusted as necessary to achieve the desired therapeutic effect. It should be noted that the ranges of effective doses provided herein are not intended to limit the invention and represent preferred dose ranges. The most preferred dosage will be tailored to the individual subject, as is understood and determinable by one of ordinary skill in the art without undue experimentation.

The concentration of the taxane in a liquid pharmaceutical composition is preferably between about 0.01 mg and about 10 mg per ml of the composition, more preferably between about 0.1 mg and about 7 mg per ml, even more preferably between about 0.5 mg and about 5 mg per ml, and most preferably between about 1.5 mg and about 4 mg per ml. Relatively low concentrations are generally preferred because the taxane is most soluble in the solution at low concentrations. The concentration of the taxane in a solid pharmaceutical composition for oral administration is preferably between about 5 weight % and about 50 weight %, based on the total weight of the composition, more preferably between about 8 weight % and about 40 weight %, and most preferably between about 10 weight % and about 30 weight %.

In one embodiment, solutions for oral administration are prepared by dissolving a taxane in any pharmaceutically acceptable solvent capable of dissolving the compound (e.g., ethanol or methylene chloride) to form a solution. An appropriate volume of a carrier which is a solution, such as Cremophor® EL solution, is added to the solution while stirring to form a pharmaceutically acceptable solution for oral administration to a patient. If desired, such solutions can be formulated to contain a minimal amount of, or to be free of, ethanol, which is known in the art to cause adverse physiological effects when administered at certain concentrations in oral formulations.

In another embodiment, powders or tablets for oral administration are prepared by dissolving a taxane in any pharmaceutically acceptable solvent capable of dissolving the compound (e.g., ethanol or methylene chloride) to form a solution. The solvent can optionally be capable of evaporating when the solution is dried under vacuum. An additional carrier can be added to the solution prior to drying, such as Cremophor® EL solution. The resulting solution is dried under vacuum to form a glass. The glass is then mixed with a binder to form a powder. The powder can be mixed with fillers or other conventional tabletting agents and processed to form a tablet for oral administration to a patient. The powder can also be added to any liquid carrier as described above to form a solution, emulsion, suspension or the like for oral administration.

Emulsions for parenteral administration can be prepared by dissolving a taxane in any pharmaceutically acceptable solvent capable of dissolving the compound (e.g., ethanol or methylene chloride) to form a solution. An appropriate volume of a carrier which is an emulsion, such as Liposyn® II or Liposyn® III emulsion, is added to the solution while stirring to form a pharmaceutically acceptable emulsion for parenteral administration to a patient. If desired, such emulsions can be formulated to contain a minimal amount of, or to be free of, ethanol or Cremophor® solution, which are known in the art to cause adverse physiological effects when administered at certain concentrations in parenteral formulations.

Solutions for parenteral administration can be prepared by dissolving a taxane in any pharmaceutically acceptable solvent capable of dissolving the compound (e.g., ethanol or methylene chloride) to form a solution. An appropriate volume of a carrier which is a solution, such as Cremophor® solution, is added to the solution while stirring to form a pharmaceutically acceptable solution for parenteral administration to a patient. If desired, such solutions can be formulated to contain a minimal amount of, or to be free of, ethanol or Cremophor® solution, which are known in the art to cause adverse physiological effects when administered at certain concentrations in parenteral formulations.

If desired, the emulsions or solutions described above for oral or parenteral administration can be packaged in IV bags, vials or other conventional containers in concentrated form and diluted with any pharmaceutically acceptable liquid, such as saline, to form an acceptable taxane concentration prior to use as is known in the art.

The taxanes of Formula 1 may be obtained by treatment of a β-lactam with an alkoxide having the taxane tetracyclic nucleus and a C(13) metallic oxide substituent to form compounds having a β-amido ester substituent at C(13) (as described more fully in Holton U.S. Pat. No. 5,466,834), followed by removal of the hydroxy protecting groups. The β-lactam corresponds to Formula (3):

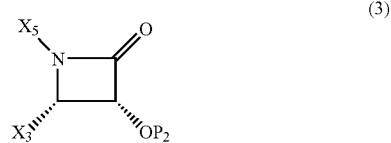

(3)

wherein $P_2$ is a hydroxy protecting group, $X_3$ is furyl and $X_5$ is t-butoxycarbonyl and the alkoxide corresponds to Formula (4):

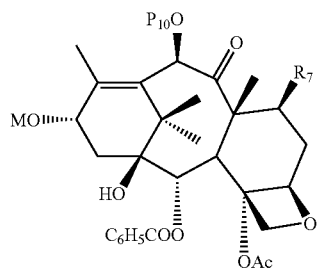

(4)

wherein M is a metal or ammonium, $P_{10}$ is a hydroxy protecting group and $R_7$ is as previously defined.

Alkoxide 4 may be prepared from 10-deacetylbaccatin III (or a derivative thereof) by selective protection of the C(10) hydroxyl group, esterification of the C(7) hydroxyl group, and then treatment with a metallic amide. In one embodiment of the present invention, the C(10) hydroxyl group of 10-deacetylbaccatin III is selectively protected with a silyl group using, for example, a silylamide or bissilyamide as a silylating agent. Preferred silylating agents include tri(hydrocarbyl)silyl-trifluoromethylacetamides and bis tri(hydrocarbyl)-silyltrifluoromethylacetamides (with the hydrocarbyl moiety being substituted or unsubstituted alkyl or aryl) such as N,O-bis-(trimethylsilyl) trifluoroacetamide, N,O-bis-(triethylsilyl)trifluoroacetamide, N-methyl-N-triethylsilyltrifluoroacetamide, and N,O-bis(t-butyldimethylsilyl)trifluoro-acetamide. The silylating agents may be used either alone or in combination with a catalytic amount of a base such as an alkali metal base. Alkali metal amides, such as lithium amide catalysts, in general, and lithium hexamethyldisilazide, in particular, are preferred. The solvent for the selective silylation reaction is preferably an ethereal solvent such as tetrahydrofuran. Alternatively, however, other solvents such as ether or dimethoxyethane may be used. The temperature at which the C(10) selective silylation is carried out is not narrowly critical. In general, however, it is carried out at 0° C. or greater.

Selective esterification of the C(7) hydroxyl group of a C(10) protected taxane can be achieved using any of a variety of common acylating agents including, but not limited to, substituted and unsubstituted carboxylic acids and carboxylic acid derivatives, e.g., carboxylic acid halides, anhydrides, dicarbonates, isocyanates and haloformates. In one embodiment, for example, the C(7) hydroxyl group of the 10-protected-10-deacteyl baccatin III is selectively acylated with 2-benzyloxypropionic acid to provide 7-(2-benzyloxypropionyl)-10-protected-10-deacetyl baccatin III which, in turn, is treated with HF or other suitable acid to provide 7-(2-hydroxypropionyl-10-protected-10-deacetyl baccatin III. In general, acylation of the C(7) hydroxy group of a C(10) protected taxane are more efficient and more selective than are C(7) acylations of a 7,10-dihydroxy taxane such as 10-DAB; stated another way, once the C(10) hydroxyl group has been protected, there is a significant difference in the reactivity of the remaining C(7), C(13), and C(1) hydroxyl groups. These acylation reactions may optionally be carried out in the presence or absence of an amine base.

Upon completion of the synthesis, taxanes corresponding to Formula 1 may be isolated by recrystallization procedures that are known in the art.

Processes for the preparation and resolution of the β-lactam starting material are generally well known. For example, the β-lactam may be prepared as described in Holton, U.S. Pat. No. 5,430,160 and the resulting enantiomeric mixtures of β-lactams may be resolved by a stereoselective hydrolysis using a lipase or enzyme as described, for example, in Patel, U.S. Pat. No. 5,879,929 Patel U.S. Pat. No. 5,567,614 or a liver homogenate as described, for example, in PCT Patent Application No. 00/41204. In this embodiment in which the β-lactam is furyl substituted at the C(4) position, the β-lactam can be prepared as illustrated in the following reaction scheme:

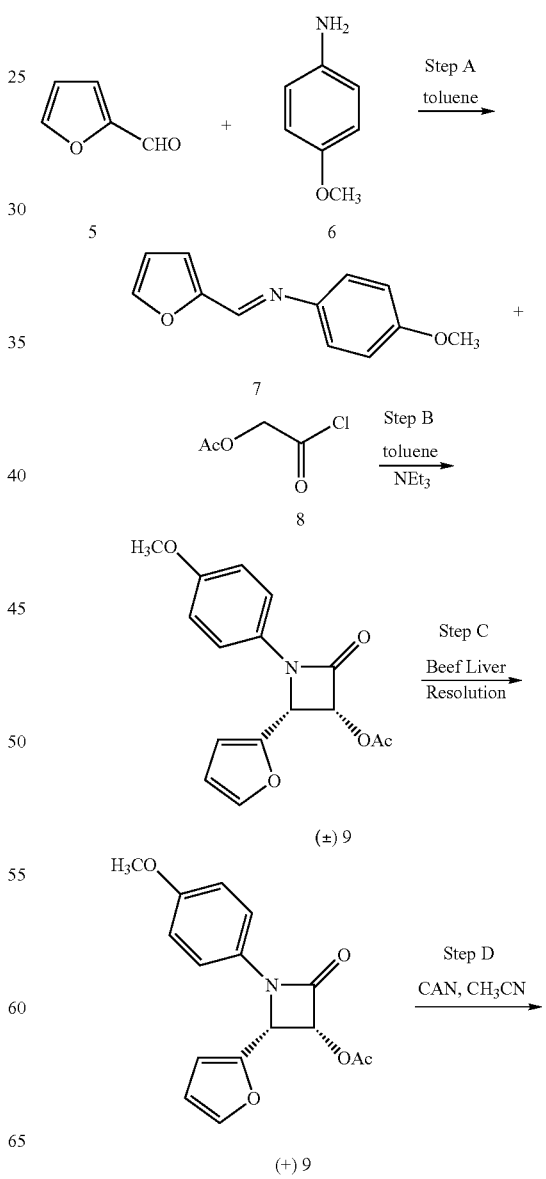

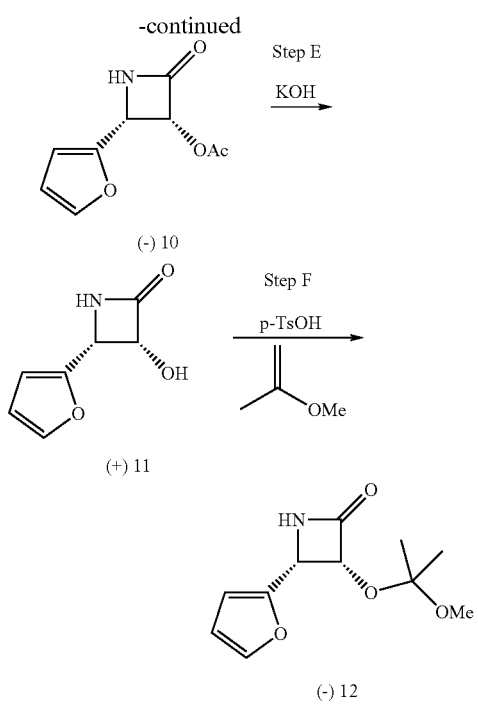

(-) 10

(+) 11

(-) 12

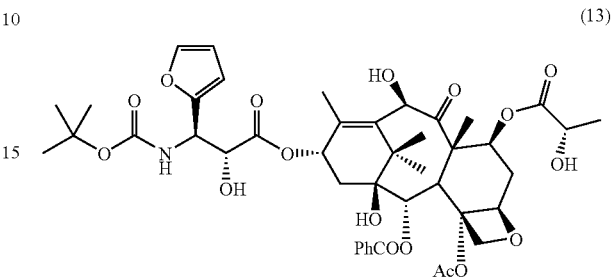

wherein Ac is acetyl, NEt₃ is triethylamine, CAN is ceric ammonium nitrate, and p-TsOH is p-toluenesulfonic acid. The beef liver resolution may be carried out, for example, by combining the enantiomeric β-lactam mixture with a beef liver suspension (prepared, for example, by adding 20 g of frozen beef liver to a blender and then adding a pH 8 buffer to make a total volume of 1 L).

DEFINITIONS

The term "acyloxy," as used herein alone or as part of another group, denotes an acyl group as described above bonded through an oxygen linkage (—O—), e.g., RC(O) O— wherein R is as defined in connection with the term "acyl."

The terms "hydroxyl protecting group" and "hydroxy protecting group" as used herein denote a group capable of protecting a free hydroxyl group ("protected hydroxyl") which, subsequent to the reaction for which protection is employed, may be removed without disturbing the remainder of the molecule. A variety of protecting groups for the hydroxyl group and the synthesis thereof may be found in "Protective Groups in Organic Synthesis" by T. W. Greene, John Wiley and Sons, 1981, or Fieser & Fieser. Exemplary hydroxyl protecting groups include methoxymethyl, 1-ethoxyethyl, benzyloxymethyl, (.beta.-trimethylsilylethoxy)methyl, tetrahydropyranyl, 2,2,2-trichloroethoxycarbonyl, t-butyl(diphenyl)silyl, trialkylsilyl, trichloromethoxycarbonyl and 2,2,2-trichloroethoxymethyl.

As used herein, "Ac" means acetyl; "Bz" means benzoyl; "t-Bu" means tert-butyl; "R" means lower alkyl unless otherwise defined; "Py" means pyridine or pyridyl; "TMS" means trimethylsilyl; "10-DAB" means 10-desacetylbaccatin III; "THF" means tetrahydrofuran; "DMAP" means 4-dimethylamino pyridine; "LHMDS" means Lithium HexamethylDiSilazanide; "CBZ" means benzyloxycarbonyl; "MOP" means methoxyphenyl; "TESCl" means triethylsilyl chloride.

The following examples illustrate the invention.

EXAMPLE 1

Synthesis of 7-((S)-(–)-2-hydroxyloxypropionyl)-2-furyl-Docetaxel (13)

10-TMS-10-DAB. To a solution of 10-DAB (25 g, 0.0459 mol) in 650 mL of THF at room temperature was added N,O-bistrimethylsilyl-trifluoromethylacetamide (9.75 mL, 0.0367 mol). The solution was cooled to −10° C. and a 1 M solution of lithium hexamethyldisilazide (2 mL) in THF was added. After 15 min, the solution was quenched with 2 mL on methanol and stirred for 10 min. The solution was treated with acetic acid (2 mmol), diluted with ethyl acetate (500 mL), warmed to room temperature, filtered through a 2 inch pad of silica gel (50 g) and concentrated under reduced pressure to give 31.5 g of white solid. Recrystallization from hot acetonitrile provided 26.3 g (93%) of the title product. m.p. 189°–191° C.; $[\alpha]_{Hg}$ −70° (CHCl₃, c=0.55). ¹H NMR (CDCl₃, 400 MHz): δ 8.11 (dd, J=8.2, 1.2 Hz, 2 H), 7.60 (tt, J=7.5, 1.2 Hz, 1 H), 7.47 (dd, J=8.2, 7.5 Hz, 2 H), 5.64 (d, J=7.2 Hz, 1 H), 5.27 (s, 1 H), 4.97 (dd, J=9.6, 2.1 Hz, 1 H), 4.84 (m, 1 H), 4.30 (d, J=8.2 Hz, 1 H), 4.25 (ddd, J=11.1, 8.6, 7.5 Hz, 1 H), 4.16 (d, J=8.2 Hz, 1 H), 4.01 (d, J=7.2 Hz, 1 H), 2.58 (ddd, J=14.4, 9.6, 7.5 Hz, 1 H), 2.28 (s, 3 H), 2.27 (m, 2 H,), 2.03 (d, J=1.3 Hz, 3 H), 1.97 (d, J=4.9 Hz, 1 H), 1.79 (ddd, J=14.4, 11.1, 2.1 Hz, 1 H), 1.68 (s, 3 H), 1.56 (s, 1H), 1.31 (d, J=8.6 Hz, 1 H), 1.16 (s, 3 H), 1.06 (s, 3 H), 0.18 (s, 9 H).

7-CBZ-10-TMS-10-DAB. To a solution of 10-trimethylsilyl 10-deacetyl baccatin III (10 g, 16.2 mmol) in 81.1 mL of anhydrous dichloromethane at 22° C. in a 250 mL round bottom flask under nitrogen charged atmosphere was added 4-dimethylamino-pyridine (4.16 g, 34.0 mmol). This was followed by a slow addition of a solution of benzyl chloroformate (4.05 mL, 28.4 mmol) in 71.1 mL of anhydrous toluene over a period of 22 hours. The reaction mixture was quenched by the addition of 1 mL of methanol. It was diluted with ethyl acetate and washed with saturated aqueous NaHCO₃ and brine. The organic layer was dried over Na₂SO₄, filtered, and evaporated to give 12.3 g of crude product, which was purified by plug filtration through flash silica gel (20 g) using 50/50 ethyl acetate/hexanes. The filtrate was evaporated to give 12.17 g of product, which was later recrystallized using ethyl acetate (1.2 mL/g) and hexanes at 1:2, to yield 12.16 g (99%) of 7-benzycarbonate 10-trimethylsilyl 10-deacetyl baccatin III. m.p. 198°–200° C. ¹H NMR (CDCl₃, 400 MHz): δ 8.10 (d, J=8.4 Hz, 2 H), 7.60 (m, 1 H), 7.47 (m, 1 H), 7.35 (m, 5 H), 5.64 (d, J=7.02 Hz, 1 H), 5.35–5.40 (m, 2 H), 5.18 (d, J=12.1 Hz, 1 H), 5.03 (d, J=11.91 Hz, 1 H), 4.95 (d, J=8.4 Hz, 1 H), 4.85 (ddd, J=13.08, 7.03 Hz, 1 H), 4.31 (d, J=8.39 Hz, 1 H), 4.15 (d, J=8.39 Hz, 1 H), 4.07 (d, J=7.03 Hz, 1 H), 2.62 (m, 1 H), 2.26–2.30 (m, 5 H), 2.10 (s, 3 H), 2.00 (d, J=4.88 Hz, 1 H), 1.93 (m, 1 H), 1.79 (s, 3 H), 1.56 (d, 1 H), 1.17 (s, 3 H), 1.05 (s, 3 H), 0.12 (s, 9 H).

7-CBZ-10-TMS-2'-MOP-3'-(2-furyl)-Docetaxel. To a solution of 7-CBZ-10-TMS-10-DAB (11.2 g, 14.9 mmol) in THF (75 mL) at −45° C. was added drop-wise a solution of LHMDS (lithium hexamethyldisilazide, 16.5 mL, 16.5 mmol) 1.0 M-titrated according to method of Irelandis: *JOC*, 1991, Vol 56, Iss 14, pp 4566–4568) in THF, over 5 min. After 1 h at −45 C, a solution of racemic cis-N-tert-butoxycarbonyl-4-(2-furyl)-3-(2-methoxy-2-propyloxy)-azetidin-2-one (12.1 g, 37.2 mmol) solution in THF (30 mL) was added to the reaction mixture over 5 min. After 1.5 h at −27 C, saturated solution of aqueous sodium bicarbonate (40 mL) was added to quench the reaction. The mixture was diluted with 300 mL of ethyl acetate and transferred to a separatory funnel and the layers separated. The aqueous layer was back extracted with ethyl acetate (100 mL×2). The organic layers were combined, dried over sodium sulfate, filtered and concentrated under reduced pressure to give 25.6 g of foam. Hexanes (120 mL) was added and triturated to collect white solid (15.2 g, 95%) by filtration. The solid was dissolved in refluxing ethyl acetate (40 mL). Hexane (120 mL) was slowly added to the solution over 10 min with stirring. Stirring was continued for 14 h. Filtration and rinsing with 20% ethyl acetate/hexane (20 mL) gave the title compound as a white solid (13.6 g, 84.8% yield). m.p. 135°–138°C. $^1$H NMR(CDCl$_3$, 400MHz): δ 8.1 (d, J=7.2 Hz, 2H), 7.6 (m, 1H), 7.44 (m, 2H), 7.42(d, J=0.8 Hz, 1H), 7.33 (m, 5H), 6.39(m,1H), 6.33 (d, J=3.2 Hz, 1H), 6.18 (dd, J=9.0, 9.0 Hz, 1H), 5.69 (d, J=6.8 Hz, 1H), 5,36 (m, 3H), 5.25 (d, J=9.8 Hz, 1H), 5.17 (d, J=6 Hz), 5.02 (d, J=6 Hz, 1H), 4.93 (d, J=8.2 Hz, 1H), 4.72 (dd, J=7.8, 2.2 Hz, 1H), 4.31 (d, J=8.4 Hz, 1H), 4.18 (d, J=8.4 Hz, 1H), 4.05 (d, J=6.9 Hz, 1H), 3.49 (s, 3H), 2.6 (m, 1H), 2.4 (s, 3H), 2.35 (m, 2H), 2.17 (s, 6H), 1.96 (m, 1H), 1.95 (s, 3H), 1.8 (s, 3H,), 1.38 (s, 9H), 1.21 (s, 3H), 1.19 (s, 3H), 0.12 (s, 9H).

10-TMS-2'-MOP-3'-(2-furyl)-Docetaxel. To a solution of 7-CBZ-10-TMS-2'-MOP-3'-(2-furyl)-Docetaxel (13.6 g) and pyridine (2 mL) in ethyl acetate (250 mL) was added 10% Pd/C (2 g). The mixture was stirred at ambient temperature under hydrogen atmosphere for 1.5 h. The mixture was filtered through a 3-inch pad of celite/silica gel using ethyl acetate and concentrated to give the title product as a white solid (11.85 g, 99%). m.p. 115°–117° C. $^1$H NMR (CDCl$_3$, 400MHz): δ 8.13 (d, J=7.2 Hz, 2H), 7.58 (m, 1H), 7.44 (m, 2H), 7.38(m, 1H), 6.32(m 1H), 6.24 (d, J=3.1 Hz, 1H), 6.18 (1H), 5.62 (1H), 5.30 (m, 2H), 5.20(s, 1H), 4.94 (m, 2H), 4.71(m, 1H), 4.36 (d, J=9.2 Hz, 1H), 4.18–4.23 (m, 1H), 4.17 (d, J=9.3 Hz, 1H), 3.91 (d, J=6.1 Hz, 1H), 2.80 (s, 3H), 2.55–2.60 (m, 1H), 2.43 (s, 3H), 2.16–2.32 (m, 2H), 1.82 (s, 3H), 1.78 (m, 1H), 1.61 (s, 3H), 1.34 (bs, 9H), 1.26 (s, 3H), 1.08 (bs, 6 H), 0.20 (s, 9H).

7-((S)-(−)-2-benzyloxypropionyl)-10-TMS-2'-MOP-3'-(2-furyl)-Docetaxel. To a solution of 10-TMS-2'-MOP-3'-(2-furyl)-Docetaxel (1.41 g, 1.49 mmol), (S)-(−)-2-benzyloxypropionic acid (0.65 g, 3.6 mmol) and 4-dimethylaminopyridine (189 mg,1.55 mmol) in pyridine (7.5 mL) was added 1-(3-dimethylaminopropyl)-3-ethylcarbodiimide hydrochloride (115 mg, 0.6 mmol). The mixture was stirred at room temperature for 14 h, diluted with ethyl acetate (100 mL) and washed with aqueous saturated sodium bicarbonate (30 mL×2). The organic layer was dried over anhydrous sodium sulfate and concentrated under reduced pressure to give 1.85 g of gum, which was directly used for the next step. $_1$H NMR(CDCl$_3$, 400 MHz): d 8.11 (d, J=7.2 Hz, 2H), 7.6 (m, 1H), 7.5 (m, 2H), 7.4 (bs, 1H), 7.3 (m, 5H), 6.31 (m, 1H), 6.21 (d, J=3.1 Hz, 1H), 6.1 (dd, J=9.0, 8.7 Hz, 1H), 5.72 (d, J=6.8 Hz, 1H), 5.55 (m, 1H), 5.45 (s, 1H), 5.3 (m, 2H), 5.15 (d, J=9 Hz, 1H), 4.91 (d, J=9 Hz, 1H), 4.90 (m, 1H), 4.71 (bs,1H), 4.21 (dd, J=13.9, 7.0 Hz, 2H), 4.06 (d, J=6.8 Hz, 1H), 2.8 (s, 3H), 2.50 (s, 3H), 2.51 (m, 1H), 2.35 (m, 2H), 1.96 (m, 1H), 1.95 (s, 3H), 1.78 (s, 3H), 1.55 (s, 3H) 1.38 (s, 9H), 1.30 (s, 3H), 1.19 (d, J=7.2 Hz, 3H), 1.18 (s, 3H), 0.12 (s, 9H).

7-((S)-(−)-2-hydroxyloxypropionyl)-2-furyl-Docetaxel. To a solution of 7-((S)-(−)-2-benzyloxypropionyl)-10-TMS-2'-MOP-3'-(2-furyl)-Docetaxel (1.85 g) in acetonitrile (20 mL) and pyridine (10 mL) at 0° C. was added drop-wise 48% aqueous HF (10 mL). The solution was stirred at room temperature for 6 h, diluted with ethyl acetate (150 mL), washed with water (70 mL×2), washed with aqueous saturated sodium bicarbonate (50 mL), dried over anhydrous sodium sulfate and concentrated under reduced pressure to give 1.45 g of gum. To a solution of the gum prepared above in 2-propanol (100 mL) was added 20% palladium hydroxide (1 g). The mixture was stirred at room temperature for 4.5 h under hydrogen atmosphere, filtered through celite pad and concentrated under reduced pressure to give 1.1 g of gum. Column chromatography (50% and 63% ethyl acetate/hexane) provide 650 mg of the title compound which was recrystallized from hot CH$_2$Cl$_2$/hexane (4/1) to give 450 mg of pure material having the structural formula (13). m.p. 174°–176° C. Anal. Calcd. for C$_{44}$H$_{55}$NO$_{17}$ 1/2H$_2$O: C, 60.13; H, 6.42. Found C, 60.14; H, 6.44. $_1$H NMR(CDCl$_3$, 400 MHz): d 8.11 (d, J=7.5 Hz, 2H), 7.62 (m, 1H), 7.5 (m, 2H), 7.42 (bs, 1H), 6.38 (m, 1H), 6.34 (d, J=3.2 Hz, 1H), 6.23 (dd, J=9.0, 8.7 Hz, 1H), 5.69 (d, J=7.2 Hz, 1H), 5.56 (m, 1H), 5.35 (d, J=11.6 Hz, 1H), 5.29 (d, J=2.0 Hz, 1H), 5.25 (d, J=11.6 Hz, 1H), 4.95 (d, J=2.2 Hz, 1H), 4.72 (dd, J=5.8, 1.9 Hz, 1H), 4.35 (d, J=8.8 Hz, 1H), 4.21 (m, 2H), 4.13 (d, J=6.7Hz, 1H), 3.97 (d, J=1.7Hz, 1H), 3.3 (d, J=5.8 Hz, 1H), 2.58 (m, 2H), 2.42 (s, 3H), 2.35 (m, 1H), 1.96 (m, 1H), 1.95 (s, 3H), 1.87 (s, 3H,), 1.38 (s, 9H), 1.21 (s, 3H), 1.19 (s, 3H).

EXAMPLE 2

Synthesis of 7-((R)-(+)-2-hydroxyloxypropionyl)-2-furyl-Docetaxel

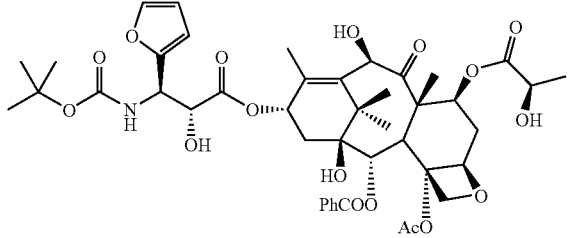

(14)

The procedure of Example 1 was repeated, except that R-(+)-2-benzyoloxypropionic acid was substituted for S-(−)-2-benzyoloxypropionic acid.

7-((R)-(+)-2-benzyloxypropionyl)-10-TMS-2'-MOP-3'-(2-furyl)-Docetaxel. To a solution of 10-TMS-2'-MOP-3'-(2-furyl)-Docetaxel (1.175 g, 1.25 mmol) in anhydrous dichloromethane (7.5 mL) was added 4-dimethylaminopyridine (226 mg,1.85 mmol). After homogeneous solution appeared, (R)-(+)-2-benzyloxy propionic acid (0.42 g, 1.85 mmol) and dicyclohexyl carbodiimide (0.644 g, 3.125 mmole) were added. The mixture was stirred at room temperature for 30 min, diluted with ethyl acetate (100 mL) and washed with aqueous saturated sodium bicarbonate (30 mL×2). The organic layer was dried over anhydrous sodium sulfate, filtered through a 2 inch pad of silica gel and concentrated under reduced pressure to give 1.57 g of gum, which was directly used for the next step. $_1$H NMR(CDCl$_3$, 400 MHz): d 8.11 (d, J=7.2 Hz, 2H), 7.6 (m, 1H), 7.5 (m, 2H), 7.4 (bs,1 H), 7.3 (m, 5H), 6.31 (m, 1H), 6.21 (d, J=3.1 Hz, 1H), 6.1 (dd, J=9.0, 8.7 Hz, 1H), 5.72 (d, J=6.8 Hz, 1H), 5.45 (m, 1H), 5.41 (s, 1H), 5.3 (m, 2H), 5.15 (d, J=9 Hz, 1H), 4.91 (d, J=9 Hz, 1H), 4.85 (m, 1H), 4.71 (bs, 1H), 4.21 (dd, J=13.9, 7.0 Hz, 2H), 4.06 (d, J=6.8 Hz, 1H), 2.8 (s, 3H), 2.50 (s, 3H), 2.47 (m, 1H), 2.35 (m, 2H), 1.96 (m, 1H), 1.95 (s, 3H), 1.78 (s, 3H), 1.55 (s, 3H) 1.38 (s, 9H), 1.30 (s, 3H), 1.19 (d, J=7.2 Hz, 3H), 1.18 (s, 3H), 0.12 (s, 9H).

7-((R)-(+)-2-hydroxyloxypropionyl)-2-furyl-Docetaxel.

To a solution of 7-((R)-(+)-2-benzyloxypropionyl)-10-TMS-2'-MOP-3'-(2-furyl )-Docetaxel (1.57 g) in acetonitrile (5 mL) and pyridine (5 mL) at 0° C. was added drop-wise 48% aqueous HF (2.5 mL). The solution was stirred at room temperature for 16 h, diluted with ethyl acetate (100 mL), washed with water (50 mL×2), washed with aqueous saturated sodium bicarbonate (50 mL), dried over anhydrous sodium sulfate and concentrated under reduced pressure to give 1.35 g of gum.

To a solution of the gum prepared above in ethyl acetate (20 mL) was added 10% Pd/C (81 mg). The mixture was stirred at room temperature for 30 min under hydrogen atmosphere, filtered through celite pad and concentrated under reduced pressure to give 1.09 g of gum. Column chromatography (40/60/1 ethyl acetate/hexane/methanol) provide 905 mg of the title compound containing 10% of S isomer.

To a solution of the compound prepared above (R/S=10) in pyridine (8 mL) at −10° C. was added drop-wise TESCI (0.086 mL, 0.51 mmole). The solution was stirred at −10° C. for 1 h, diluted with ethyl acetate (80 mL), washed with aqueous saturated sodium bicarbonate (50 mL), dried over anhydrous sodium sulfate and concentrated under reduced pressure to give 870 mg of gum. Column chromatography (65/35 ethyl acetate/hexane) provided 370 mg of the title compound having the structural formula (14) and containing 5% of S isomer. m.p. 161°–163° C. $_1$H NMR (CDCl$_3$, 400 MHz): d 8.11 (d, J=7.5 Hz, 2H), 7.62 (m, 1H), 7.5 (m, 2H), 7.42 (bs, 1H), 6.38 (m, 1H), 6.34 (d, J=3.2 Hz, 1H), 6.23 (dd, J=9.0, 8.7 Hz, 1H), 5.69 (d, J=7.2 Hz, 1H), 5.55 (m, 1H), 5.35 (d, J=11.6 Hz, 1H), 5.29 (d, J=2.0 Hz, 1H), 5.25 (d, J=11.6 Hz, 1H), 4.90 (d, J=2.2 Hz, 1H), 4.72 (s, 1H), 4.35 (d, J=8.8 Hz, 1H), 4.21 (m, 2H), 4.13 (d, J=6.7 Hz, 1H), 3.97 (d, J=1.7 Hz, 1H), 3.3 (d, J=5.8 Hz, 1H), 2.58 (m, 2H), 2.42 (s, 3H), 2.35 (m, 1H), 1.96 (m, 1H), 1.95 (s, 3H), 1.87 (s, 3H,), 1.39 (s, 3H) 1.38 (s, 9H), 1.21 (s, 3H), 1.19 (s, 3H).

EXAMPLE 3

In Vitro Cytotoxicity Measured by the Cell Colony Formation Assay

Four hundred cells (HCT116) were plated in 60 mm Petri dishes containing 2.7 mL of medium (modified McCoy's 5a medium containing 10% fetal bovine serum and 100 units/mL penicillin and 100 g/mL streptomycin). The cells were incubated in a CO$_2$ incubator at 37° C. for 5 h for attachment to the bottom of Petri dishes. The compound identified in Example 1 was made up fresh in medium at ten times the final concentration, and then 0.3 mL of this stock solution was added to the 2.7 mL of medium in the dish. The cells were then incubated with drugs for 72 h at 37° C. At the end of incubation the drug-containing media were decanted, the dishes were rinsed with 4 mL of Hank's Balance Salt Solution (HBSS), 5 mL of fresh medium was added, and the dishes were returned to the incubator for colony formation. The cell colonies were counted using a colony counter after incubation for 7 days. Cell survival was calculated and the values of IC$_{50}$ (the drug concentration producing 50% inhibition of colony formation) were determined for each tested compound.

An identical assessment was carried out using the VM46 colon cell line.

The assays described above were repeated using the compound identified in Example 2. The results of these assays are tabulated below in comparison with data for paclitaxel and docetaxel.

| Compound | IN VITRO IC$_{50}$ (nM) HCT116 | IN VITRO IC$_{50}$ (nM) VM46 |
|---|---|---|
| Paclitaxel | 2.1 | 20.0 |
| Docetaxel | 0.6 | 6.7 |
| 7-((S)-(−)-2-hydroxyloxypropionyl)-2-furyl-docetaxel | 0.17 | 2.5 |
| 7-((R)-(+)-2-hydroxyloxypropionyl)-2-furyl-docetaxel | 0.05 | 4.22 |

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above products and methods without departing from the scope of the invention, it is intended that all matter contained in the above description and shown in the accompanying drawing shall be interpreted as illustrative and not in a limiting sense.

What is claimed is:

1. A composition comprising an isolated taxane having the formula:

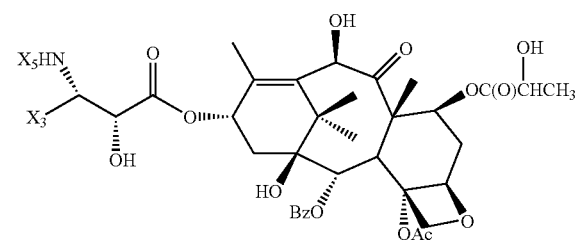

wherein
   X$_3$ is furyl,
   X$_5$ is t-butoxycarbonyl,
   Bz is benzoyl, and
   Ac is acetyl.

2. The composition of claim 1 wherein $X_3$ is 2-furyl.

3. The composition of claim 2 wherein the composition comprises a diastereomic mixture of 7-((S)-(−)-2-hydroxyloxy-propionyl)-2-furyl-docetaxel and 7-((R)-(+)-2-hydroxyloxypropionyl)-2-furyl-docetaxel.

4. The composition of claim 3 wherein the mixture is a racemic mixture of 7-((S)-(−)-2-hydroxyloxypropionyl)-2-furyl-docetaxel and 7-((R)-(+)-2-hydroxyloxy-propionyl)-2-furyl-docetaxel.

5. The composition of claim 3 wherein the molar ratio of the diastereomers in the mixture is at least 5:1.

6. The composition of claim 3 wherein the molar ratio of the diastereomers in the mixture is at least 10:1.

7. The composition of claim 3 wherein the molar ratio of the diastereomers in the mixture is at least 20:1.

8. The composition of claim 1 wherein the taxane is in crystalline form.

9. A method of preparing the composition of claim 1, the method comprising crystallizing the taxane from a solution.

10. A pharmaceutical composition comprising a therapeutically effective amount of the composition of claim 1 and at least one pharmaceutically acceptable carrier.

11. The pharmaceutical composition of claim 10 wherein the composition is in liquid form.

12. The pharmaceutical composition of claim 10 wherein the composition is a solid.

13. The pharmaceutical composition of claim 10 wherein the composition is in a dosage unit form.

14. A method for preparing a medicament, the method comprising mixing a composition of claim 1 with a non-aqueous, pharmaceutically acceptable solvent.

15. A method of inhibiting colon tumor growth in a mammal, said method comprising administering a therapeutically effective amount of a pharmaceutical composition of claim 13.

16. The method of claim 15, wherein the pharmaceutical composition is administered orally.

17. The method of claim 15, wherein the pharmaceutical composition is administered parenterally.

18. An isolated taxane having the formula:

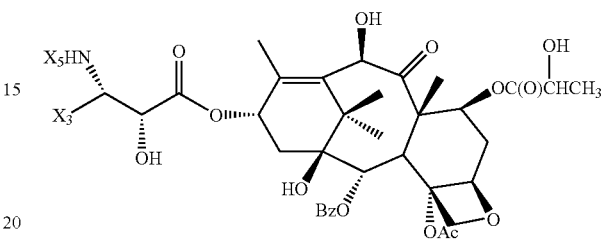

wherein
$X_3$ is furyl,
$X_5$ is t-butoxycarbonyl,
Bz is benzoyl, and
Ac is acetyl.

19. The taxane of claim 18 wherein $X_3$ is 2-furyl.

* * * * *